(12) United States Patent
Deb et al.

(10) Patent No.: US 8,546,092 B2
(45) Date of Patent: Oct. 1, 2013

(54) ONE STEP NANOSENSOR FOR SINGLE AND MULTIDRUG RESISTANCE IN ACUTE CORONARY SYNDROME (ACS)

(75) Inventors: Suryyani Deb, Asansol (IN); Anjan Dasgupta, Kolkata (IN); Prabir Lahiri, Kolkata (IN)

(73) Assignee: University of Calcutta, Kolkata (IN)

( * ) Notice: Subject to any disclaimer, the term of this patent is extended or adjusted under 35 U.S.C. 154(b) by 466 days.

(21) Appl. No.: 12/632,437

(22) Filed: Dec. 7, 2009

(65) Prior Publication Data

US 2011/0053172 A1 Mar. 3, 2011

(30) Foreign Application Priority Data

Aug. 25, 2009 (IN) .......................... 1095/KOL/2009

(51) Int. Cl.
*G01N 33/00* (2006.01)
*G01N 31/00* (2006.01)
*G01N 33/553* (2006.01)
*A61K 49/00* (2006.01)

(52) U.S. Cl.
USPC .......... 435/7.24; 436/517; 436/518; 436/525; 436/10; 436/35; 436/55; 436/56; 436/69; 436/811; 435/7.21; 424/9.2

(58) Field of Classification Search
USPC ............. 435/7.2, 7.24, 69.6, 287.2; 436/518, 436/524, 525, 546, 10, 35, 55, 56, 69, 811, 436/517; 424/9.2
See application file for complete search history.

(56) References Cited

PUBLICATIONS

Deb et al. Role of purinergic receptors in platelet-nanoparticle interactions, Nanotoxicology 1 (1-4): 92-102 (Mar.-Dec. 2007).*
Semberova et al. Carbon Nanotubes Activate Platelets by Facilitating Extracellular Calcium Influx. Blood: ASH Annual Meeting Abstracts: 112: Abstract 992 (2008).*
Wiviott et al., Clopidogrel Resistance: A New Chapter in a Fast-Moving Story, Circulation, Journal of the American Heart Association, 2004, vol. 109, pp. 3064-3067.
Aleil, B. et al., "Flow cytometric analysis of intraplatelet VASP phosphorylation for the detection of clopidogrel resistance in patients with ischemic cardiovascular diseases," J. Thromb. Haemost., 2005, vol. 3, pp. 85-92.
Daniel, M.C. et al., "Gold nanoparticles: assembly, supramolecular chemistry, quantum-size-related properties, and applications toward biology, catalysis, and nanotechnology," Chem. Rev., 2004, vol. 104, pp. 293-346.
Deb, S. et al., "Role of purinergic receptors in platelet-nanoparticle interactions," Nanotoxicology, Mar.-Dec. 2007, vol. 1, pp. 92-102.
Jana, N.R. et al., "Seeding Growth for Size Control of 5-40 nm Diameter Gold Nanoparticles," Langmuir, 2001, vol. 17, pp. 6782-6786.
Turkevich, J., et al., "A study of the nucleation and growth processes in the synthesis of colloidal gold," Discuss. Faraday Soc., 1951, vol. 11, pp. 55-75.
Wikipedia webpage, "Plasmon," printed on May 10, 2011, retrieved from the internet: URL<http://en.wikipedia.org/wiki/Plasmon>, 4 pages.

* cited by examiner

*Primary Examiner* — Gail R Gabel
(74) *Attorney, Agent, or Firm* — Foley & Lardner LLP

(57) ABSTRACT

An embodiment relates to a method of detecting a drug resistance in a patient comprising adding nanoparticles to sample platelets to form activated platelets containing the nanoparticles and comparing a difference in activation of the activated platelets and the sample platelets. Another embodiment relates to a method of monitoring a thrombotic risk factor in a subject in a general population comprising adding nanoparticles to sample platelets to form activated platelets containing the nanoparticles and comparing a difference in activation of the activated platelets and the sample platelets. Yet another embodiment relates to a kit comprising nanoparticles, a fluorescence dye tagged antibody and optionally a buffer, wherein the kit is configured to detect a drug resistance in a patient or a likelihood of the thrombotic risk factor in a subject in general population.

7 Claims, 7 Drawing Sheets

Figure 1: a (top); b (bottom)
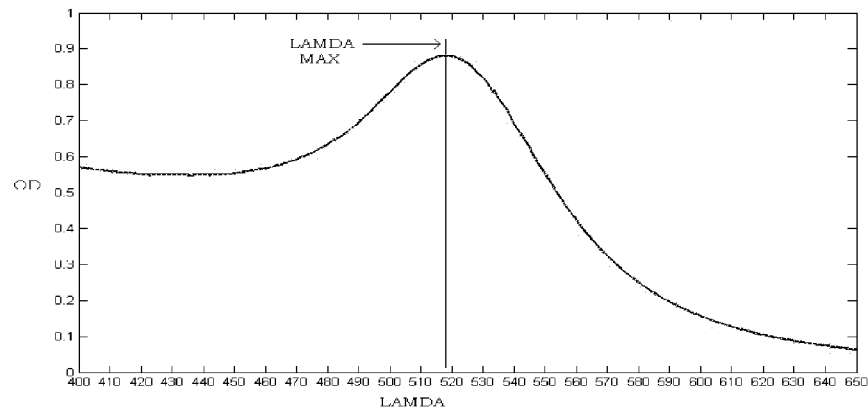
| | | Diam. (nm) | % Intensity | Width (nm) |
|---|---|---|---|---|
| Temperature (°C): 25.0 | | | Duration Used (s): 50 | |
| Count Rate (kcps): 174.1 | | | Measurement Position (mm): 4.65 | |
| Cell Description: Disposable low volume cuvette (100ul) | | | Attenuator: 9 | |
| | | Diam. (nm) | % Intensity | Width (nm) |
|---|---|---|---|---|
| Z-Average (d.nm): 19.28 | Peak 1: | 21.23 | 97.6 | 7.696 |
| PdI: 0.181 | Peak 2: | 4311 | 2.4 | 960.6 |
| Intercept: 0.810 | Peak 3: | 0.000 | 0.0 | 0.000 |
| Result quality : Good | | | | |
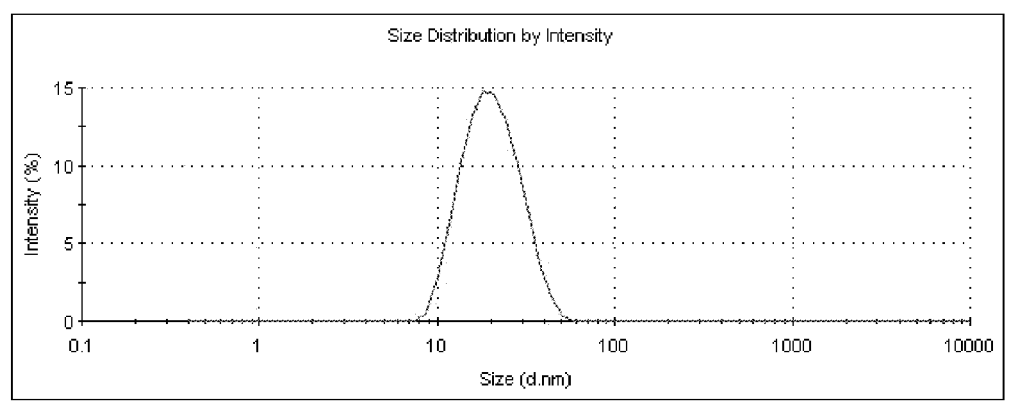

Figure 4: a (top), b, c and d (bottom)
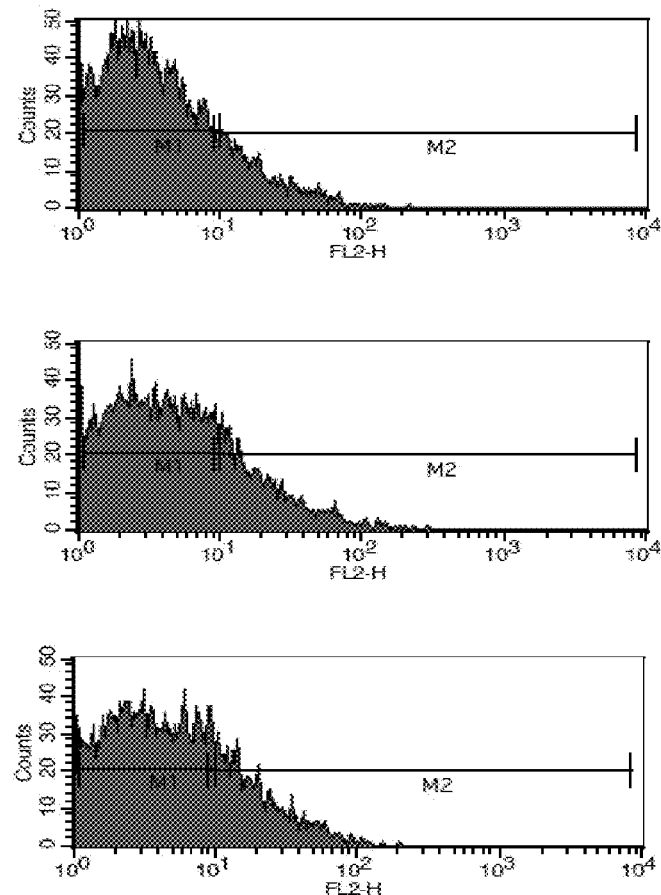
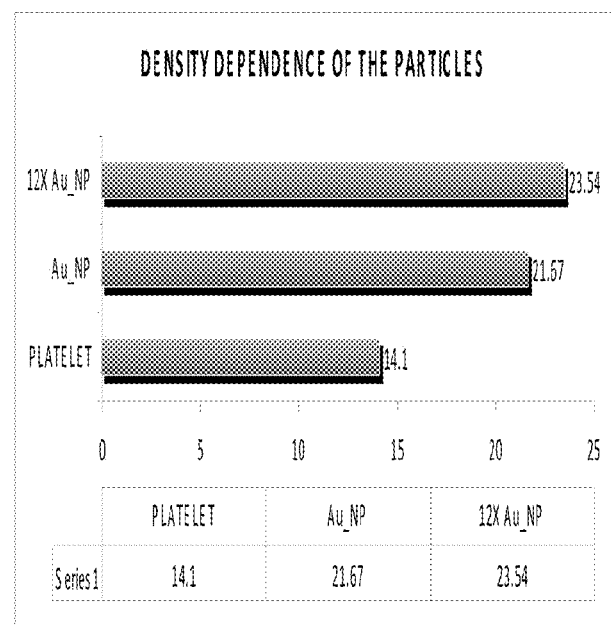

ONE STEP NANOSENSOR FOR SINGLE AND MULTIDRUG RESISTANCE IN ACUTE CORONARY SYNDROME (ACS)

CROSS-REFERENCE TO RELATED APPLICATIONS

The present application claims the benefit of Indian Patent Application No. 1095/KOL/2009, filed Aug. 25, 2009, which is hereby incorporated by reference in its entirety.

BACKGROUND

Acute coronary syndrome (ACS) is a leading cause of death in the world. ACS is an umbrella term used to cover any group of clinical symptoms compatible with acute myocardial ischemia. Acute myocardial ischemia is chest pain due to insufficient blood supply to the heart muscle that results from coronary artery disease (also called coronary heart disease).

Platelets are known to play an important role in ACS. Platelets, or thrombocytes, are small, irregularly-shaped anuclear cells (i.e., cells that do not have a nucleus containing DNA), 2-4 μm in diameter, which are derived from fragmentation of precursor megakaryocytes. The average lifespan of a platelet is between 8 and 12 days. Platelets play a fundamental role in hemostasis and are a natural source of growth factors. They circulate in the blood of mammals and are involved in hemostasis, leading to the formation of blood clots.

If the number of platelets is too low, excessive bleeding can occur (hemorrhage). However, if the number of platelets is too high, blood clots can form (thrombosis), which may obstruct blood vessels and result in such events as a stroke, heart attack, pulmonary embolism or the blockage of blood vessels to other parts of the body, such as the extremities of the arms or legs.

The function of platelets is the maintenance of haemostasis. This is achieved primarily by the formation of platelet aggregate, when damage to the endothelium of blood vessels occurs. On the converse, thrombus (platelet aggregate in patho-physiological condition) formation must be inhibited at times when there is no damage to the endothelium. Thrombus formation is generally associated with activation of the platelets.

Platelet activation involves changes to platelet metabolic biochemistry, shape, surface receptors, and/or membrane phospholipid orientation. Platelet activation involves a series of morphologic and functional changes in the platelets. Changes to platelet metabolic biochemistry result from substances generated by the platelet itself as well as cells in the blood vessels. Substances that induce platelet activation are called agonists. Each agonist attaches to a specific receptor on/inside the platelet, causing a series of reactions inside of the platelet.

The inner surface of blood vessels is lined with a thin layer of endothelial cells. Under this is a layer of collagen. Under normal physiological conditions, collagen does not pass into the bloodstream as endothelial cells produce a protein called von Willebrand factor (vWF), a cell adhesion ligand, which helps endothelial cells adhere to collagen. When the endothelial layer is injured, the collagen is exposed.

When the platelets contact collagen, they are activated. They are also activated by thrombin and adenosine diphosphate (ADP). They can also be activated by a negatively-charged surface, such as glass.

Platelet activation further results in the scramblase-mediated transport of negatively-charged phospholipids to the platelet surface. These phospholipids provide a catalytic surface (with the charge provided by phosphatidylserine and phosphatidylethanolamine) for the tenase and prothrombinase complexes.

Activated platelets change in shape to become more spherical, and pseudopods form on their surface. Thus they assume a stellate (star-like) shape.

Following platelet activation, platelets can aggregate, or clump together to form a hemostatic plug, using fibrinogen and vWF as a connecting agent. Platelet adhesion is generally the initial step in the formation of the hemostatic plug. Activated platelets will adhere, via glycoprotein (GP) Ia, to the collagen that is exposed by endothelial damage. Aggregation and adhesion act together to form the platelet plug. The most abundant platelet aggregation receptor is glycoprotein (GP) IIb/IIIa; this is a calcium-dependent receptor for fibrinogen, fibronectin, vitronectin, thrombospondin, and von Willebrand factor (vWF). Myosin and actin filaments in platelets are stimulated to contract during aggregation, further reinforcing the plug.

Clinical trials have shown that aspirin and clopidogrel help prevent myocardial infarction, stroke, and cardiovascular death. Aspirin and clopidogrel are believed to inhibit the production of chemicals responsible for platelet activation. For example, an activator and mediator of many leukocyte functions, including platelet aggregation, inflammation, and anaphylaxis, is platelet-activating factor, a potent phospholipid also known as a PAF, PAF-acether or AGEPC (acetyl-glyceryl-ether-phosphorylcholine).

For normal subjects that do not exhibit ACS, platelets are inactivated and would show resting behavior (unless the subject is emotionally stressed or in any other abnormal physiological condition). On the other hand, for subjects who are ACS risk prone, but unaware of it and not taking aspirin and/or clopidogrel, the platelets will be in the activated state. The subjects who are ACS risk prone, but aware of it and taking aspirin and/or clopidogrel, the platelets would likely be in a lowered activated state if the subject is not resistant to aspirin and/or clopidogrel.

Clopidogrel is recommended for the management of ACS. This along with aspirin, is recommended in the American College of Cardiology/American Heart Association guideline. It is also used along with aspirin, during the placement of coronary artery stents. Clopidogrel resistance was recognized in such procedures, as several patients did not have the anticipated platelet aggregation response to an ex vivo adenosine diphosphate challenge. This assessment can be made by individual aggregometric studies. Failure to obtain a deaggregation profile in a patient treated with clopidogrel at a reasonable ADP concentration (10 um) would normally considered as a signature for drug resistance.

From the EXCELSIOR study, which investigated the phenomenon, it was appreciated that it was present prior to treatment with clopidogrel and was therefore an intrinsic property of the patient's platelet (information is available on the worldwide web).

A study relating to clopidogrel versus aspirin in patients at risk of ischaemic events (CAPRIE) revealed a statistically significant 8.7% (P=0.043) relative risk reduction in stroke, myocardial infarction, or ischaemic death in patients treated with clopidogrel in comparison to aspirin. The resistance to either of the drugs is therefore an important field of study. The dosage specification of the drugs also varies in different countries as different doses are recommended. The variation in population makes the proper assessment of drug resistance variability in population difficult.

In many cases dual antiplatelet drug therapy is used for patient safety. Despite the benefits of dual antiplatelet therapy, many patients continue to suffer adverse consequences (thrombus formation) of cardiovascular disease as they may be actually resistant to such drugs. It is thus important to have a quick sensor that will firstly assess the resistance to aspirin or clopidogrel in patients in one step and secondly assess the equivalence of the drug effects with respect to variations in geographic populations (which may correspond to genetic variations of patient population) and variations in licensed manufacturer of the drugs.

The conventional kit of drug resistance (e.g., using the PLT VASP/P2Y12 Test kit manufactured by BD) as described in Aleil et al. J. Thromb Haemost. 2005, 3, 85-92, is specific to clopidogrel resistance.

Corgenix Medical (CONX), a Denver diagnostic test-kit maker, has developed AspirinWorks to help doctors identify those not likely to benefit from a daily aspirin dose. A report on the test's efficacy was presented in July by independent Canadian and Australian researchers at a meeting of the International Society on Thrombosis & Haemostasis.

Neither of these kits can, however, find out whether there is single or multiple drug resistance as they are specific to individual drug. Therefore, it would be desirable to develop a method that may enable a quick assessment of (a) a patient's drug resistance single or multiple drugs, (b) a subject's risk assessment to ACS and (c) equivalence of drug potency with respect to geographic genetic or manufacturer variations.

SUMMARY

The embodiments herein relate to nanotechnology based sensing of platelet function and its aberrations in cardiac diseases.

An embodiment relates to a method of detecting a drug resistance in a patient comprising adding nanoparticles to sample platelets to form activated platelets containing the nanoparticles and comparing a difference in activation of the activated platelets and the sample platelets. The method could further comprise treating the activated platelets with a fluorescence tagged antibody.

Preferably, a lack of a substantial difference in activation of the activated platelets and the sample platelets indicates likelihood of the drug resistance in the patient. Preferably, the antibody comprises CD62P, the CD62P is expressed on a surface of the activated platelets. Preferably, a relative expression of the CD62P expressed on the surface of the activated platelets is a measure of the drug resistance in the patient. Preferably, the method is configured to detect the drug resistance in the patient to a single or multiple drugs for acute coronary syndrome (ACS). Preferably, the nanoparticles comprise particles having particle sizes in a range of about 1 nm to about 100 nm, about 10 nm to about 50 nm, about 15 nm to about 25 nm, or about 18 nm to about 20 nm. Preferably, the drug resistance is to a drug comprising clopidogrel, aspiring or combinations thereof.

Another embodiment relates to a method of monitoring a thrombotic risk factor in a subject in a general population comprising adding nanoparticles to sample platelets to form activated platelets containing the nanoparticles and comparing a difference in activation of the activated platelets and the sample platelets. Preferably, an indication of a lack of a substantial difference in activation of the activated platelets and the sample platelets indicates likelihood of the thrombotic risk factor in the subject.

Another embodiment relates to a kit comprising nanoparticles, a fluorescence dye tagged antibody and optionally a buffer, wherein the kit is configured to detect a drug resistance in a patient or a likelihood of the thrombotic risk factor in a subject in general population. Preferably, the drug resistance is to a drug comprising clopidogrel, aspiring or combinations thereof. Preferably, the antibody comprises fluorescence dye tagged CD62P. Preferably, a degree of the fluorescence dye tagged CD62P expressed on a surface of activated platelets is a measure of the drug resistance in the patient. Preferably, the kit is configured to detect the drug resistance in the patient to a single or multiple drugs for acute coronary syndrome (ACS). Preferably, the nanoparticles comprise particles having particle sizes in a range of about 1 nm to about 100 nm, about 10 nm to about 50 nm, about 15 nm to about 25 nm, or about 18 nm to about 20 nm.

The kit could further comprise instructions for detecting the drug resistance in the patient, the instructions comprising adding nanoparticles to sample platelets to form activated platelets containing the nanoparticles and comparing a difference in activation of the activated platelets and the sample platelets. Preferably, a lack of a substantial difference in activation of the activated platelets and the sample platelets indicates likelihood of the drug resistance in the patient.

The kit could further comprise instructions for monitoring a thrombotic risk factor in a subject in a general population, the instructions comprising adding nanoparticles to sample platelets to form activated platelets containing the nanoparticles and comparing a difference in activation of the activated platelets and the sample platelets. Preferably, an indication of a lack of a substantial difference in activation of the activated platelets and the sample platelets indicates likelihood of the thrombotic risk factor in the subject.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1: (a) is the plasmon spectrum of gold nanoparticle. Lambda is the wavelength of light expressed in nanometers. OD is the corresponding absorbance (dimensionless); (b) dynamic light scattering study showing the nanoparticle size (the light scattering studies being performed in NANO ZS 80 Malvern instruments). The atomic concentration of nanoparticles was 20 μM. The measurement was performed following the principle of dynamic light scattering, which measures the time decay of autocorrelation function of scattered light. The decay follows an exponential pattern and the logarithmic slope of the curve provides the diffusion coefficient of the particle which in turns measures the estimate of the particle size. The NANO ZS 80 Malvern instrument diagram can be found on the world wide web).

FIG. 4a, b and c show the distribution of the CD62P, wherein the figures show that nanoparticles enhance the CD62P expression for a normal individual.

(FIG. 3 data is evaluated using an approximate 4% cut off of this set of fluorescence (FL2, ordinate) and forward scattering (FSC abscissa) phase points.

DETAILED DESCRIPTION

Figure 2A:
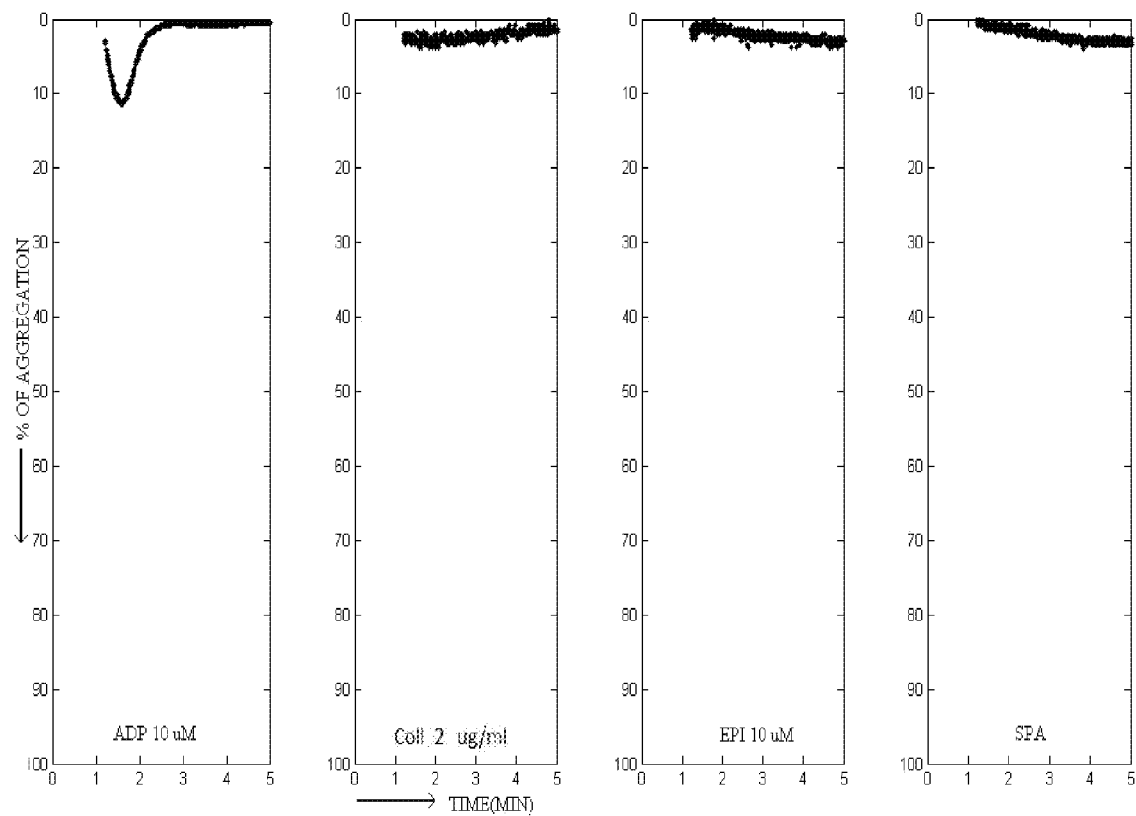
FIG. 2a shows the aggregometry profile of double responders. The aggregometry was performed using Chronlog aggregometer in PRP (platelet rich plasma). The platelet study was performed using the agonists ADP, collagen and epinephrine. SPA represented the spontaneous aggregation profile (the molarity indicated in the figure). As no considerable aggregation was observed in any of the patients it is implied that the patient responded to both the drugs (aspirin and clopidogrel).

The embodiments relate to a one step method to sense multi-drug resistance in ACS (acute coronary syndrome) patients. Sensing in the embodiments herein is used in a broader platform than making a diagnosis. When a patient acquires (or genetically possesses) resistance to more than one drug for a given disease (e.g., acute coronary syndrome), the state is termed as multidrug-resistance.

Other embodiments relate to a method for determining subjects in a general population that are prone to risk of ACS. Yet, other embodiments relate to a kit for undertaking the methods of the embodiments herein.

Normally the evaluation of drug resistance in ACS patients is an elaborate procedure in which independent aggregometric studies needs to be performed. In the embodiments of the one-step methods herein, the results can be performed using a simpler experimental set up in which nanoparticle can be added in platelet suspension, and then labeled with antibody. Differential level of changes in the CD62P level provides whether a given patient is single responder, double responder or double resistant to two drugs aspirin and clopidogrel.

Preferably, the nanoparticle comprises a noble-metal containing nanoparticle. Noble metal refers to the metals of groups 9, 10 and 11 of transition metal series in the periodic table (of the IUPAC style). The noble metal of the noble-metal containing nanoparticle includes rhodium, iridium, palladium, silver, osmium, iridium, palladium, platinum, gold or combinations thereof.

Nanoparticle refers to a particle having at least one dimension sized between 1 and 100 nanometers.

Considering the abundance of ACS and large scale occurrence of multi drug resistance the method may prove to be patient friendly, fast and quantitative. Furthermore it may be useful even for testing the resistance or sensitivity to hitherto untested drugs used for similar purpose.

The principle of the methods herein is simple. If the drug does not respond in a patient having ACS, the platelet will remain pre-activated and the addition of the nanoparticle would not substantially activate the platelet. If the drug does respond in a patient having ACS, then the platelet will be inactivated (in resting behavior) and the addition of the nanoparticle would substantially activate the platelet.

If a subject does not know whether he has ACS and does not take the drug, the platelet will be inactivated if the subject does not have ACS. Subsequently, the addition of the nanoparticle would substantially activate the platelet. On the other hand, if a subject does not know whether he has ACS and does not take the drug, the platelet will be activated if the subject does have ACS. Subsequently, the addition of the nanoparticle would not substantially activate the platelet.

The incremental activation in response to the nanoparticle is likely to be lesser as the nanoparticle (as seen in the clopidogrel or aspirin case) can activate more if platelet responds to the drug and the platelet would be in an inactivated state. If the untested drug has no response on a patient having ACS, there will be an absence of or substantially little incremental CD62P expression, for example, which measures the degree of activation in the embodiments herein, and reverse will be the case if there is a good response on the patient having ACS to the drug.

In the embodiments herein, nanoparticles have been used as a sensor in diverse ways, the most common being from their color change (altered plasmonic response) or their change in other physical properties like fluorescence, electrical conductivity, magnetic or semiconductor properties. The term "sensor" refers to the biocatalytic property of the noble metal nanoparticle such as a gold nanoparticle to activate platelets, and this property is used in the sensing method of the embodiments herein.

The embodiments herein use a biologically induced property of the nanomaterial, namely its prothrombotic effect as on platelets to arrive at the prognosis of drug resistance patients having ACS or of a subject in the determination of the risk of having ACS. The prothrombogenic properties of gold and other metallic nanoparticles was first reported by the inventors in "Role of Purinergic Receptors in Platelet nanoparticle interaction." See Suryyani Deb Mohor Chatterjee, Jaydeep Bhattacharya, Prabir Lahiri, Utpal Chaudhuri, Sankar Pal Choudhuri, Saumitra Kar, Om Parkash Siwach, Prasenjit Sen and Anjan. Kr. Dasgupta. *Nanotoxicology.* 2007; 1(2):93-103. Optical aggregometry, impedance aggregometry, CD62P expression, plate and cone assay can be used to measure the prothombotic effects of nanoparticles on platelets.

Among ACS patients the ones showing resistance to the conventional antiplatelet drugs (e.g., aspirin or clopidogrel) respond differentially to such nanoparticle as compared to ones who respond to it. The other impact of the embodiments herein is the comparative assessment of different antiplatelet drugs from different companies claiming equivalence. The method being quantitative can be used as a measure of potential equivalence of two identical/equivalent antiplatelet drugs manufactured by two different companies and how the resistance to patients vary when such equivalent drugs are used.

Imagine that a company X is selling clopidogrel with a given brand name. The test using according the embodiments herein method can be similar to the one for untested drugs. The patient has to be treated with the reference drug and company X's drug in alternative week. If platelet activation as measured by the CD62P expression, for example, is elevated with nanoparticle only with the reference drug, it is likely that company X's drug is not equivalent to the reference drug.

However, is substantial platelet activation is not measured with both reference drug and company X's drug, it is possible to conclude that the patient is likely a drug resistant subject.

Among the different sizes of nanoparticles that were synthesized (about 10-50 nm), it was found that the activation effect is particularly marked using a smaller nanoparticle, preferably about 18-22 nm. The higher size nanoparticles produced similar activation but to a lower extent.

The example embodiment described below was arrived at while investigating the toxic effects of nanoparticles using platelet aggregometry and flow cytometry. However, nanoparticle toxicity is not an issue using noble metal nanoparticles such as gold nanoparticles which are not known to exhibit toxic effect unlike the effect induced by carbon nanotube, which can aggregate in the absence of any agonist.

In the example embodiment, gold nanoparticle induced pre-activation is used as a diagnostic tool applied under ex vivo condition (in which patient is not in touch with the administered nanoprobe) and therefore no toxicity issue is relevant here. Gold is one of the safest nanoparticle to handle. Flow cytometry and aggregometry are techniques to measure this activation and aggregation process ex vivo for the sake of diagnosis of the platelet function of the patient.

EXAMPLES

In the example embodiment, the method can be as follows.

Platelets were isolated by differential centrifugation from fresh human blood. Briefly, blood was collected in an anticoagulant 3.2% sodium citrate (9 ml fresh blood in 1 ml anticoagulant) and centrifuged at 180 g for 20 min. PRP (platelet-rich plasma) was incubated for 15 min at 37° C. Platelets are isolated by sepharose 2B column. Cells were washed in HEPES buffer (10 mM Hepes, 137 mM NaCl, 16.8 mM KCl, 2 mM $MgCl_2$, 1 mM$CaCl_2$, 0.119 mM $NaHCO_3$, pH 7.4). The platelet suspension ($2$-$10^8$ cells in 1 mL) was then incubated at 37° C. for 5 min with stirring in the presence of gold nanoparticles, (20 μM, 22 nm hydrodynamic diameter as measured by dynamic light scattering), Cells were then washed and incubated with 2 μL PE-labeled antibody against CD62P for 60 min in ice in the dark followed by the addition of an equal amount of 2% paraformaldehyde for 30 min. Cells were then washed and resuspended in same HEPES buffer. Samples were again washed with PBS and analyzed in a Becton Dickinson FACSCalibur flow cytometer. The relative expression of CD62P was then evaluated for the said dosage of nanoparticle The mechanism of drug resistance of platelet to different antiplatelet drugs (e.g., clopidogrel, aspirin) is dependent on different physiological and genetic properties. Aggregative response of patients responding (or not responding) to antiplatelet drugs (e.g., aspirin) depended largely on the resistance of such patients to the said drugs. But interestingly it was observed that the pro-aggregatory activation response of platelets using nanoparticle of a certain size (18-20 nm) had the greatest dependence on the clinical state of the patients on aspirin or clopidogrel regimen. In flow cytometric studies, conditions were maintained such that there are no agonists, and therefore no aggregation caused by agonists. But activation was still observed reflected by the CD62P expression. There is believed to be a barrier between activation and aggregation. Aggregation can occur when this barrier is crossed.

The Malvern DLS instrument used to measure the nanoparticle size provides (a) intensity average (b) weight average (c) number average. The intensity average was closest to the raw data and therefore the nanoparticle size numbers reported in the application are the intensity average diameter. In most cases, however, the TEM determined diameter was slightly less than the intensity average diameter.

The differential effects on platelets was verified using the platelet signaling response at various stages using appropriate antibody in absence and presence of the nanoparticles and a discriminatory response was observed only in the latter case. If the platelet is already activated, nanoparticle is unlikely to activate it further. In an ACS patient who has drug resistance, the incremental activity is therefore less likely than a patient who is a responder to the drug.

The results of the example embodiment are presented below.

FIG. 1a shows the plasmon spectrum of a gold nanoparticle used in the example embodiment. FIG. 1b shows the size spectrum gold nanoparticles, wherein the size of the gold nanoparticles was determined by dynamic light scattering studies.

The FIG. 1a shows the plasmon behavior of citrate capped nanoparticle. The Plasmon behavior is a well known signature of collective electronic oscillation realizable in the nanoscale systems in response to an incident electromagnetic wave. The plasmon resonance for precious metals appears at visible wavelength. For gold nanoparticles the typical wavelength is between 515-540 nm depending on the size of the nanoparticle (smaller the size lower is the wavelength). The citrate capping on the gold nanoparticles could be a thin absorbed layer of citrate on the gold nanoparticle. The citrate capping acts as a reducing agent and also an electrostatic capping ligand in the presence of other reducing agents e.g., $NaBH_4$ (Daniel, M. C.; Astruc, D. *Chem. Rev.* 2004, 104, 293-346, Jana, N. R.; Gearheart, L.; Murphy, C. J. *Langmuir* 2001, 17, 6782-6786; Turkevitch, J. *Discuss. Faraday Soc.* 1951, 11, 55-75). It is one of the most popular among all of the direct reduction techniques that produce aqueous Au NPs.

The FIG. 1b represents the dynamic light scattering profile that provides an estimate of the gold nanoparticle size that is most effective in inducing platelet aggregation. The dynamic light scattering test was done using citrate capped nanoparticles. The typical concentration of platelet in PRP (platelet rich plasma) was of the order of $10^6$ cells per uL. The effective size range was concluded using nanoparticles with varying size range. This could be achieved by varying the citrate concentration while synthesizing the gold nanoparticles. For each such sample, the platelet response was studied.

Figure 2B:
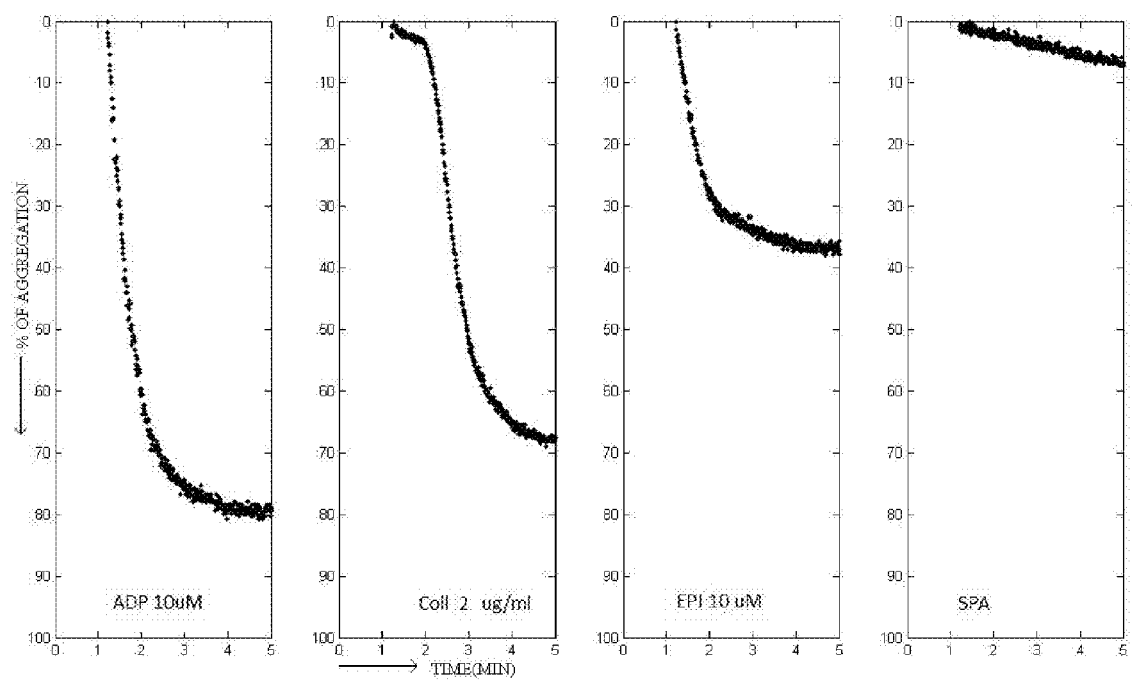
FIG. 2b shows the aggregometry profile for double resistant patients—the agonist symbols (e.g., ADP etc.) are identical to those FIG. 2a. All agonists can induce aggregation implied that the patient non responder to both the drugs (aspirin and clopidogrel).
Figure 2C:
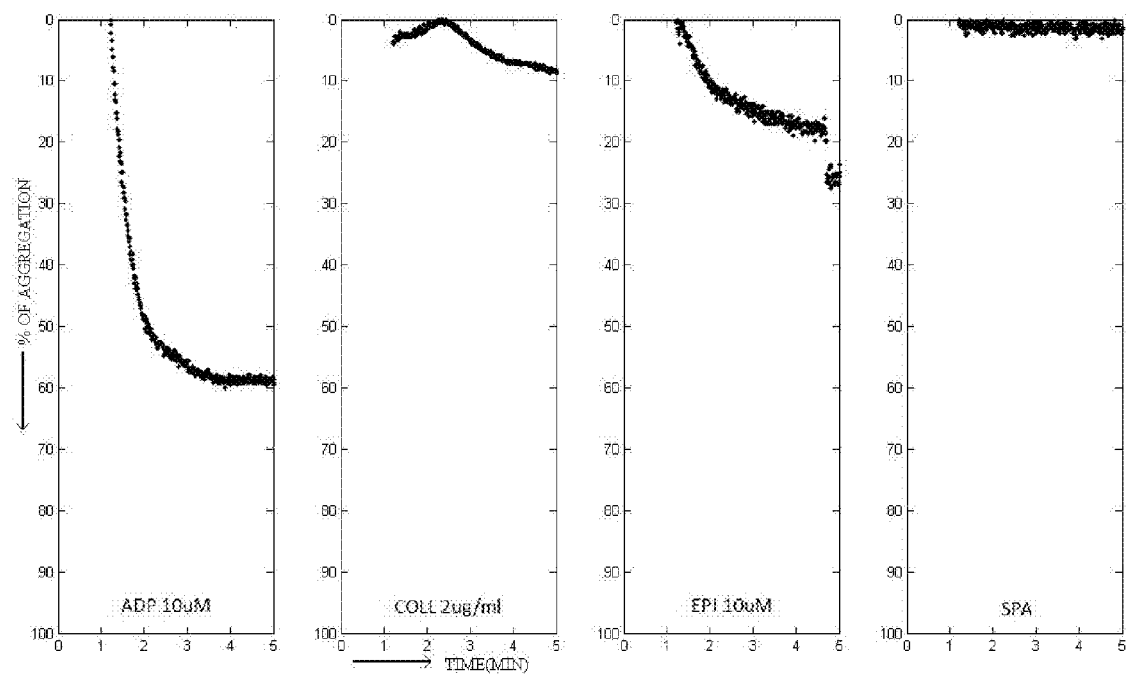
FIG. 2c shows the aggregometry profile for single responders—the agonist symbols (e.g., ADP etc.) are identical to FIG. 2a. Only ADP can induce aggregation where collagen cannot agonists implied that the patient non responder (clopidogrel) to one drug where as responder to other (aspirin).

As a comparative example, the conventional way of detecting the drug resistance involving aggregometry was undertaken. FIGS. 2a, b and c respectively represents aggregometric results in presence of the agonist ADP (non response to which implies clopidogrel resistance) and collagen (non response to which implies resistance to aspirin). FIG. 2a shows that in double responders (no aggregation in both collagen and ADP), there is effectively no aggregation even using aggregating agents such as agonist ADP and collagen. FIG. 2b shows the reverse for double resistant patients (normal aggregation in both collagen and ADP). FIG. 2c shows the response of single responders (aggregation by ADP, but no collagen induced aggregation).

Figure 3:
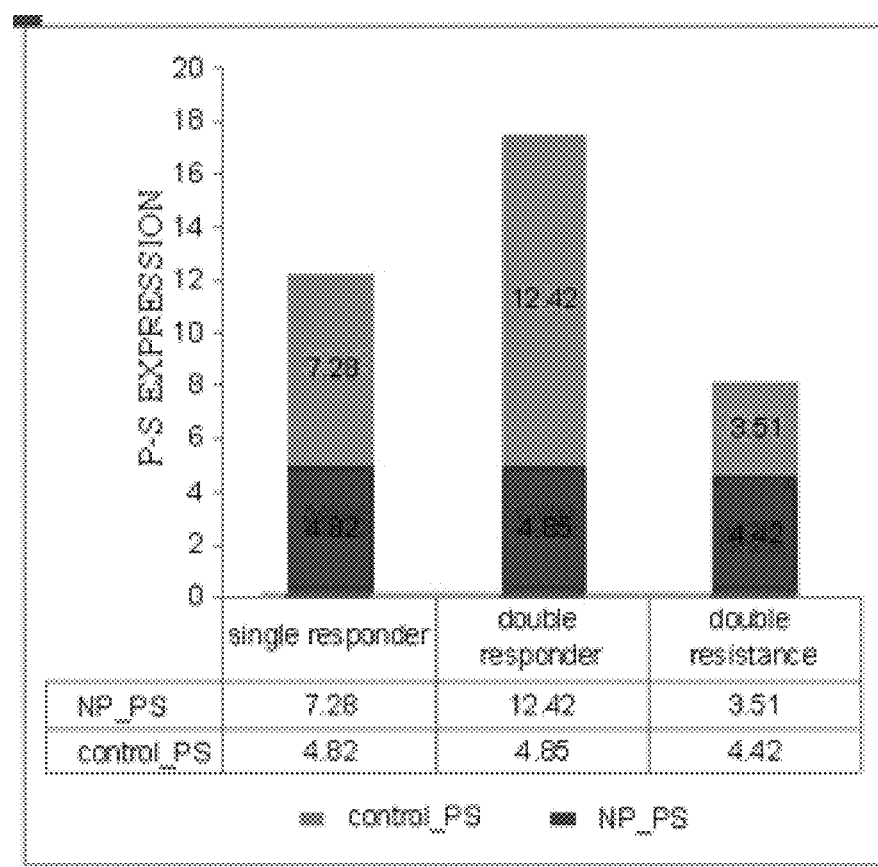
FIG. 3 shows the results of flow cytometric sensing of gold nanoparticle effect on patients undergoing standard dual drug therapy (aspirin and clopidogrel). The table entries repetitively represent the percentage of p-s expression (the % representing the fractional increase of p-s in respect to resting platelets). The darker and lighter shade respectively represents absence and presence of nanoparticles. It is evident that in absence of nanoparticles no discriminatory effect is observed in drug sensitive or drug resistant cases. On the other hand the discriminatory effect is clearly shown in the lighter shade bars that correspond to CD62P expression in presence of gold nanoparticles having atomic concentration of 20 µM. The CD62P expression was studied in the absence and presence of gold nanoparticles. In the absence of gold nanoparticles, the expressed level was arbitrarily chosen at a value close to 4%. In presence of nanoparticle, the relative increase or decrease of the expression is then noted.

FIG. 3 represents the summary of the nanoparticle induced platelet activation in different patients tested in accordance with the example embodiment. Estimation of CD-62 P or P-Selectin expression (using fluorophore tagged anti CD-62P antibody) on gold nanoparticle treated platelet surface was done as follows. The CD62P antigen is an integral membrane protein associated with alpha-granules of platelets, endothelial cells, and megakaryocytes. The CD62P antigen is expressed on the internal alpha-granule membrane of resting platelets. Upon platelet activation and granule secretion, the alpha-granule membrane fuses with the external plasma membrane and the CD62P antigen is expressed on the surface of the activated platelet.

250 µl Platelets suspension (final concentration 10*5 cell/µl) were incubated at 37° C. for 5 min without stirring in the presence of an agonist, either in the presence or absence of nanoparticles. Cells were then washed and incubated with 2 µL PE-labeled antibody against CD62P for 60 min in ice in the dark followed by the addition of an equal amount of 2% paraformaldehyde for 30 min. Cells were then washed and re-suspended in same HEPES buffer. Samples were again washed with PBS and analyzed in a Becton Dickinson FACSCalibur flow cytometer.

Followed by the addition of an equal amount of 4% paraformaldehyde for 30 min. Cells were then washed and resuspended in buffer B and incubated with 2 µL PE-labeled antibody against P-Selectin (CD62P) for 60 min in ice in the dark. Samples were again washed with PBS and analyzed in a Becton Dickinson FACSCalibur flow cytometer.

The distribution of the CD62P is explained in the FIGS. 4a, b, c and d, where it is shown that nanoparticles enhance the CD62P expression for a normal individual. The histogram illustrates that if one assumes a given cutoff count level (frequency of occurrence) there is an enhancement of CD62P expression as nanoparticle is added and then the nanoparticle concentration is enhanced 12 times. In FIGS. 4a, b and c, what is relevant here is the ratio 21:14 or 23:14 rather than the actual value of the counts itself.

Figure 5:
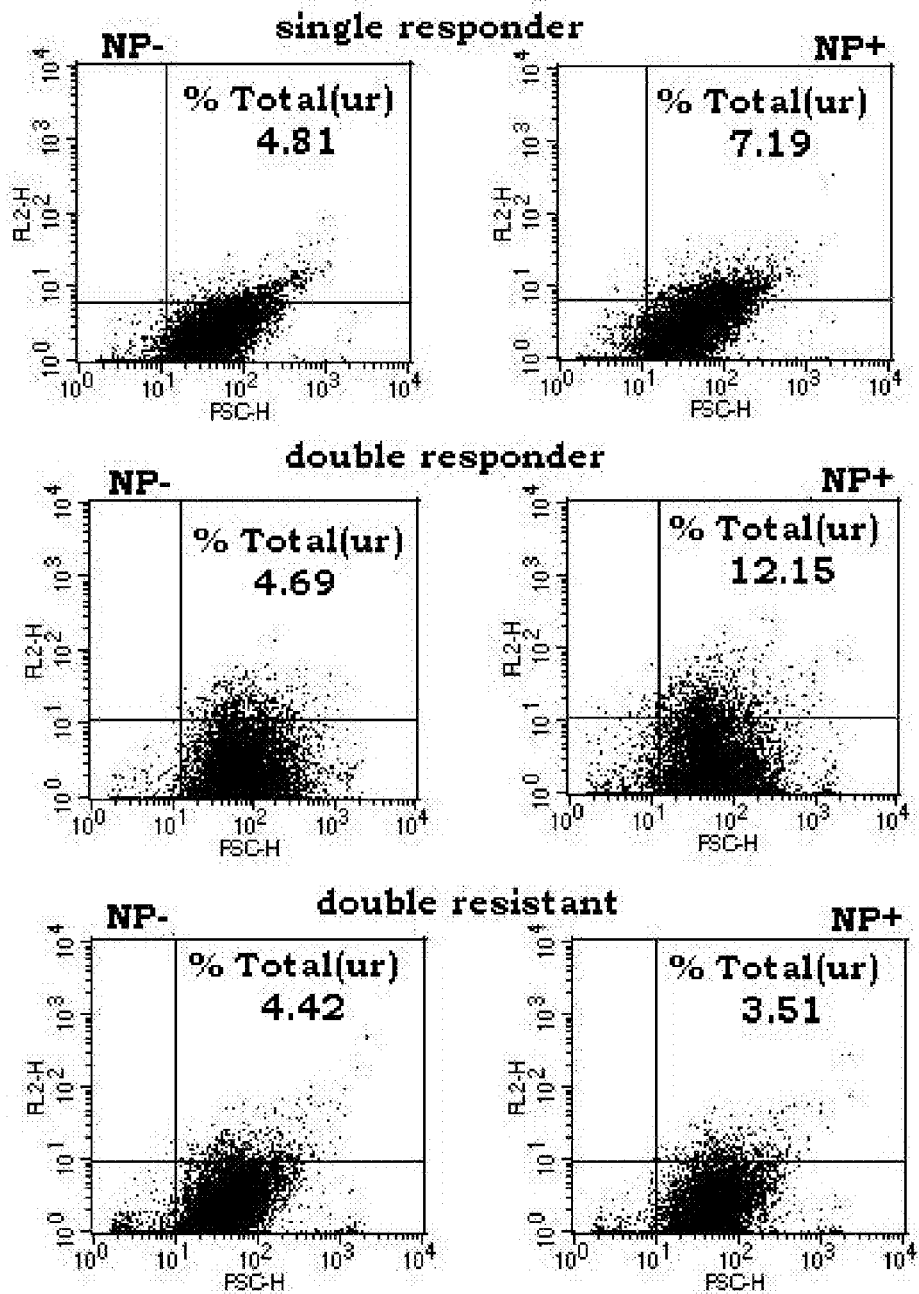
FIG. 5 shows the distribution of the CD62P, wherein differential expression of CD62P corresponds to drug resistance or drug responder.

Furthermore, the distribution of the CD62P is explained in FIG. 5 where differential expression of CD62P correspond to drug resistance or drug responder. In the case of a drug responder, the CD62P expression increased, whereas in the case of a patient having drug resistance, the CD62P expression become decreased. The left panels of FIG. 5 represent platelets without nanoparticles whereas right panels represent platelets having nanoparticles therein. The term "ur" in FIG. 5 refers to upper right quadrant.

In the example embodiment, how CD62P expression varies in different patients was not relevant. The primary aim was to find out in what ratio the nanoparticle enhances the expression of CD62P. So what was determined was how and to what extent the CD62P expression is enhanced in presence of a fixed dose of nanoparticle. For double resistant patients, the enhancement was the lowest; it was intermediate for single resistant patients; and the highest for responders. The responder behaves more or less like a normal individuals who do not suffer from ACS.

The activation is determined using flow cytometric studies in which nanoparticle is added in platelets from different patients. Nanoparticles were added at a final concentration (20 µM of gold) to the washed platelet, and Phycoerythrin (PE) conjugated anti P-Selectin or CD62P antibody was added in the resulting suspension.

In the example embodiment, the gold nanoparticles were added to a suspension containing platelets (platelet suspension) using a pipette. The platelet rich plasma, which was a concentrated platelet suspension, had a platelet concentration of $10^5$ cells per µt. The concentration was measurable using autocounter.

The term "concentration" denotes atoms per unit volume. For a given size the atoms per cc or µM of gold will represent the nanoparticles at a given size at a given density. By the term "final" means, for example, that when x µL of nanoparticle colloid with concentration C µM was added to y µL of suspension, the final colloid concentration will become $xC/(x+y)$ µM.

In the example embodiment, the CD62P antigen is an integral membrane protein associated with alpha-granules of platelets, endothelial cells, and megakaryocytes. The CD62P antigen is expressed on the internal alpha-granule membrane of resting platelets. Upon platelet activation and granule secretion, the alpha-granule membrane fuses with the external plasma membrane and the CD62P antigen is expressed on the surface of the activated platelet.

In the example embodiment, P-Selectin is a good marker for platelet activation. Using stained platelets with specific platelet alpha granule marker Phycoerythrin (PE) labeled P-Selectin (CD62P), the label indicates presence of fluorescence detectable by flow cytometry. The CD62P antigen is expressed on the internal alpha-granule membrane of resting platelets. Upon platelet activation and granule secretion, the alpha-granule membrane fuses with the external plasma membrane and the CD62P antigen is expressed on the surface of the activated platelet. When analysed by flow cytometry, one obtains a quantifiable expression for platelet activation.

Other names for P-Selectin include CD62P, Granule Membrane Protein 140 (GMP-140), and Platelet Activation-Dependent Granule to External Membrane Protein (PADGEM). In inactivated condition, the granules will not be released to the platelet surface. The CD62P binding will be absent and there will be an absence of fluorescence. Under activated conditions on the other hand, there will be a release of the granules and consequently there will be binding with the fluorescent labelled antibody. The bound antibody alone will have the contribution in the flow cytometry as the rest is washed out. Thus the flow cytometry method provides higher count if only there is activation of platelets.

Based on the results of the sample embodiment, it was seen that for patients with different degree of resistance to drugs the P-Selectin expression varied. It was minimum in case of double resistance while was maximum in case of double responder. The single responders fell in the middle region. The P-Selectin expression is defined by the ratio value of 100×CD62P(AuNP+)/CD62P(AuNP−) (expressed in %) for the activation were 250% for double responder, 150% for single responder and 79% for double resistant (see FIG. 3), wherein "CD62P(AuNP+)" means platelets pre-treated with gold nanoparticles (AuNP) and labelled with CD62P; "CD62P(AuNP−)" means platelets similarly labelled but not pre-treated with AuNP. The maximum and minimum value therefore differ by an order of magnitude (250% to 79%), with the single responder having the P-Selectin expression value of 150%.

The choice of control in each case was set at a comparable value (approximately 4%, see FIG. 3) with a goal of seeing how much amplification (or reduction) in CD62P expression occurs in the presence of gold nanoparticle. As mentioned earlier the double responder showed a 250% (100×12.82/4.85) enhancement whereas the single responder and the double resistant showed 150% (100×7.28/4.82) and 79% (100×3.51/4.42) of the control, wherein the control means the counts observed in the absence of nanoparticle as shown in FIG. 3.

Total count in each flow cytometric experiments was kept at 10,000. The total count was kept at a constant value 10,000 as this is the maximal sensitivity to which the Becton Dickinson FACSCalibur flow cytometer can be set. Each count corresponds to a single light scattering object (in this case platelet).

In the detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or, "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for detecting resistance to antiplatelet drugs in a patient diagnosed with or at risk for acute coronary syndrome (ACS) comprising:
   obtaining a platelet sample from the patient, wherein the patient is taking one or more antiplatelet drugs;
   dividing the platelet sample into a first portion of platelets and a second portion of platelets;
   contacting noble metal containing nanoparticles to the first portion of platelets;
   contacting the first and second portion of platelets with a labeled anti-CD62P antibody;
   measuring the expression of CD62P in the first portion of platelets;
   measuring the expression of CD62P in the second portion of platelets; and
   comparing the level of CD62P expression in the first portion of platelets to the level of CD62P expression in the second portion of platelets; and
   determining the patient's resistance to antiplatelet drugs, wherein a substantially higher level of CD62P expression in the first portion of platelets indicates that the subject is not resistant to the antiplatelet drug.

2. The method of claim 1, wherein a lack of a substantial difference in CD62P expression between the first portion of platelets and the second portion of platelets indicates a likelihood of drug resistance in the patient.

3. The method of claim 1, wherein the labeled anti-CD62P antibody comprises a fluorescently labeled anti-CD62P antibody.

4. The method of claim 1, wherein the method is configured to detect the antiplatelet drug resistance in the patient to a single or multiple drugs for ACS.

5. The method of claim 1, wherein the nanoparticles comprise particles having particle sizes in a range of about 1 nm to about 100 nm, about 10 nm to about 50 nm, about 15 nm to about 25 nm, or about 18 nm to about 20 nm.

6. The method of claim 1, wherein the drug resistance is to a drug comprising clopidogrel, aspirin or combinations thereof.

7. The method of claim 1, wherein the noble metal nanoparticles comprise one or more metals selected from the group consisting of: rhodium, iridium, palladium, silver, osmium, platinum and gold.

* * * * *

UNITED STATES PATENT AND TRADEMARK OFFICE
CERTIFICATE OF CORRECTION

PATENT NO. : 8,546,092 B2
APPLICATION NO. : 12/632437
DATED : October 1, 2013
INVENTOR(S) : Deb et al.

Page 1 of 1

It is certified that error appears in the above-identified patent and that said Letters Patent is hereby corrected as shown below:

In the Specification

In Column 7, Line 47, delete "nanoparticle" and insert -- nanoparticle. --, therefor.

In Column 9, Line 59, delete "µT." and insert -- µL. --, therefor.

In Column 12, Line 16, delete ""A" or," and insert -- "A" or --, therefor.

Signed and Sealed this
Eighth Day of April, 2014

Michelle K. Lee
*Deputy Director of the United States Patent and Trademark Office*